United States Patent [19]

Meathrel

[11] Patent Number: 4,826,772
[45] Date of Patent: May 2, 1989

[54] ETHYLENE OXIDE MONITORING DEVICE

[75] Inventor: William G. Meathrel, Gananoque, Canada

[73] Assignee: Graphic Controls Canada, Ltd., Ontario, Canada

[21] Appl. No.: 33,587

[22] Filed: Apr. 1, 1987

[30] Foreign Application Priority Data

Apr. 8, 1986 [CA] Canada ............................ 506118

[51] Int. Cl.[4] .......................................... G01N 31/22
[52] U.S. Cl. ...................................... 436/93; 422/57; 422/58; 436/1
[58] Field of Search ................. 436/1, 93; 422/58, 57

[56] References Cited

U.S. PATENT DOCUMENTS

| | | |
|---|---|---|
| 2,998,306 | 8/1961 | Hucyk . |
| 3,258,312 | 6/1966 | Olson . |
| 3,852,034 | 12/1974 | Gunther . |
| 3,924,219 | 12/1975 | Braun . |
| 3,950,980 | 4/1976 | Braun et al. . |
| 3,992,154 | 11/1976 | Whitbourne et al. . |
| 4,015,937 | 4/1977 | Miyamoto et al. . |
| 4,102,201 | 8/1978 | Trine et al. . |
| 4,327,575 | 5/1982 | Locker . |
| 4,407,960 | 10/1983 | Tratnyek ............................ 436/1 |
| 4,436,819 | 3/1984 | Manning ............................ 436/1 |
| 4,597,942 | 7/1986 | Meathrel ........................... 422/57 |
| 4,675,161 | 6/1987 | Hashimoto et al. ............. 436/93 X |
| 4,678,640 | 7/1987 | Hamano et al. ................. 436/93 X |

OTHER PUBLICATIONS

Loving, et al., Medical Instrumentation, 18(6), pp. 309–317.
Loving, et al., J. Hospital Supply, Processing & Distribution, Jul.-Aug. (1985), pp. 48–53.

Primary Examiner—Barry S. Richman
Assistant Examiner—Jill Johnston
Attorney, Agent, or Firm—Ratner & Prestia

[57] ABSTRACT

Monitoring exposure to ethylene oxide using a dosimeter or monitoring device avoids using devices that collect a sample for future testing or devices that must be sent away for lab analysis. The device comprises a reactive coating including a layer of activated alumina particles coated with p-nitrobenzyl pyridine and ammonium chloride, and is adapted to instantly produce a color intensity change directly related to the dosage of the reactive coating to ethylene oxide upon the addition of a developer.

43 Claims, 3 Drawing Sheets

U.S. Patent    May 2, 1989    Sheet 1 of 3    4,826,772
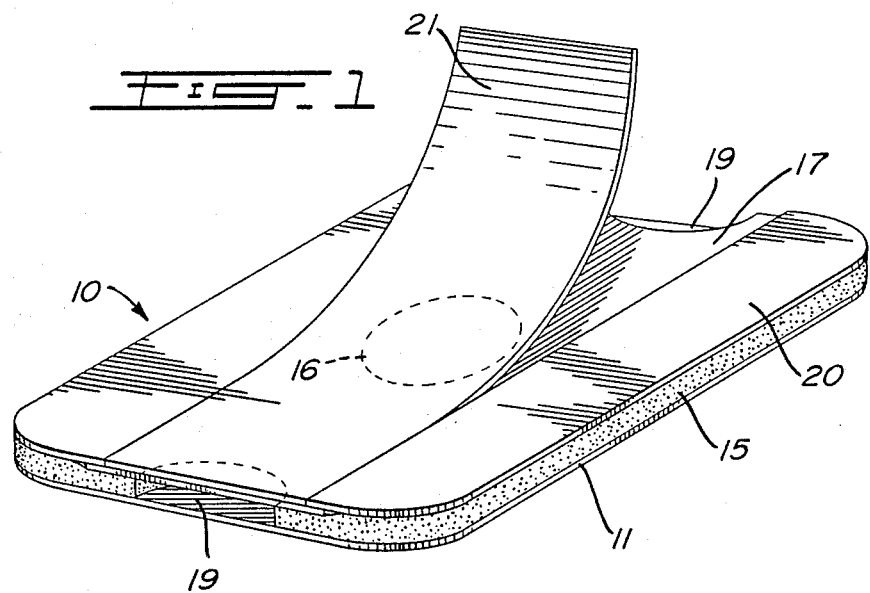
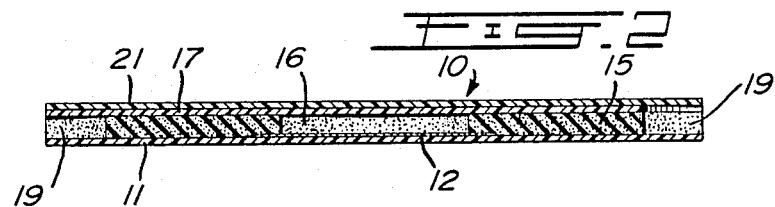
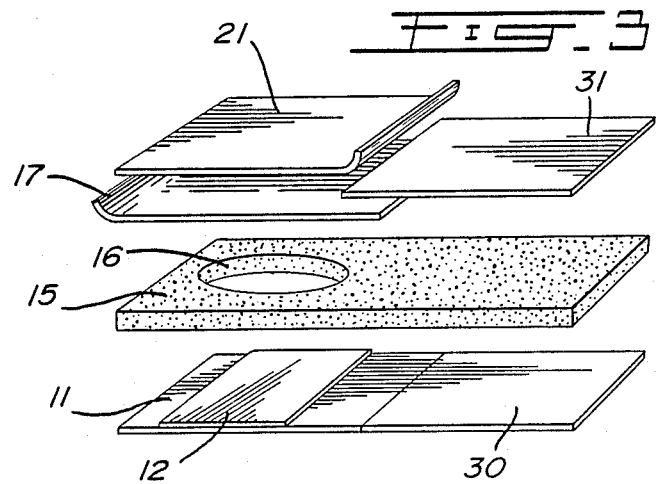

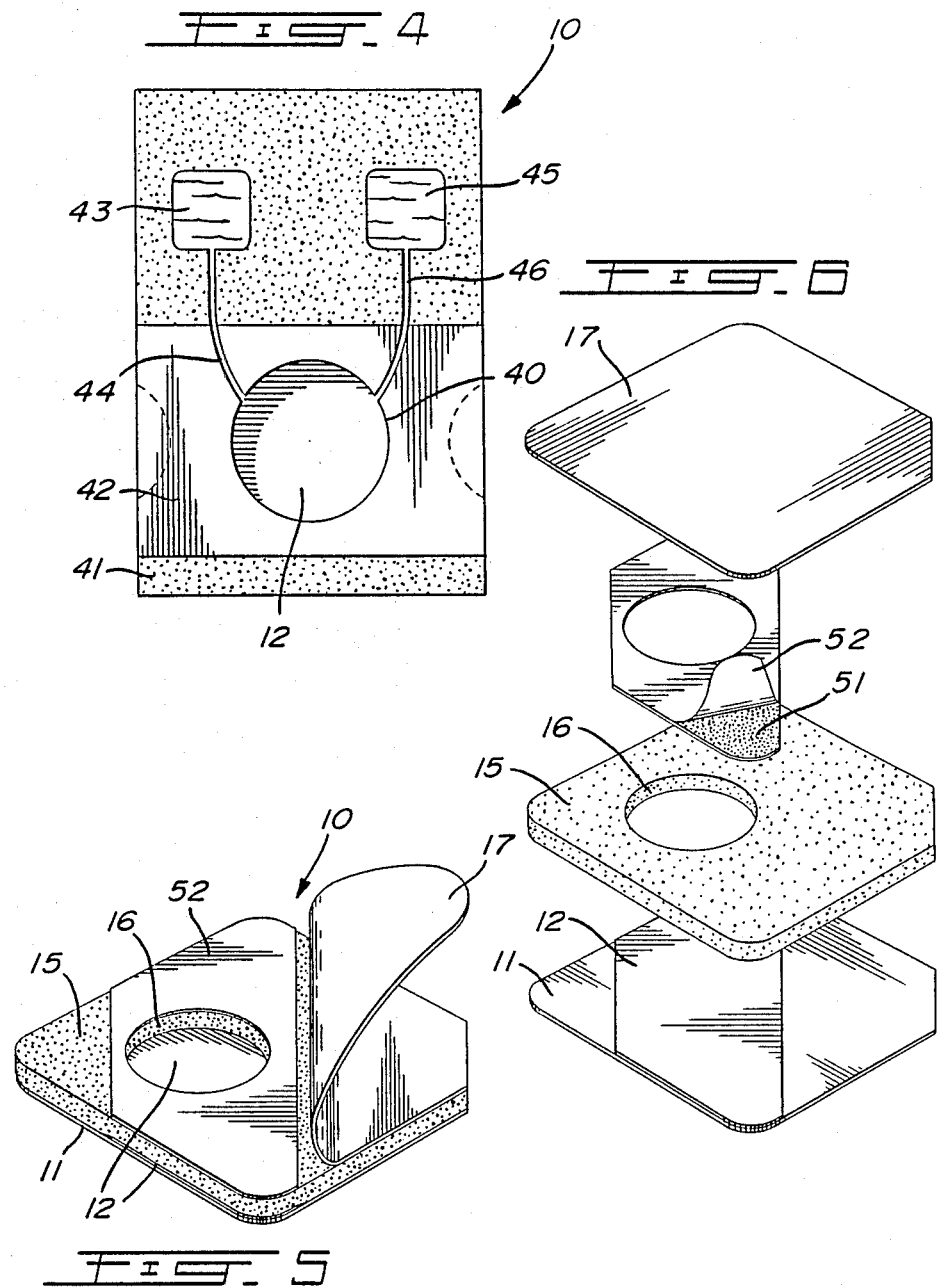

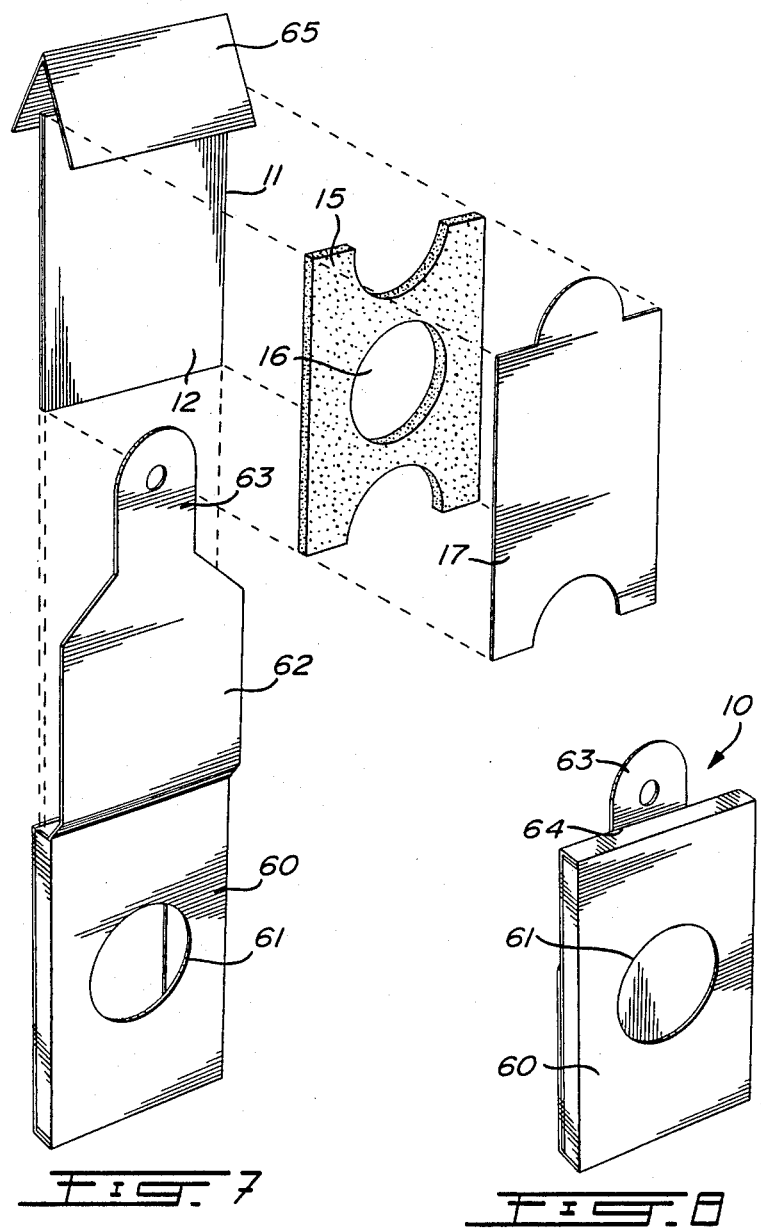

ETHYLENE OXIDE MONITORING DEVICE

The present invention relates to monitoring exposure to ethylene oxide and more specifically to a dosimeter or monitoring device to determine the time weighted average ethylene oxide concentration in an environment.

Ethylene oxide is used extensively as an intermediate in the production of chemical products such as antifreeze and surfactants. It is also used as a fumigant and as a sterilizing agent of heat sensitive goods. The effects of ethyelene oxide on the human body are not yet fully known. There is, however, a consensus that exposure to ethylene oxide is dangerous and should be minimized. On June 22nd, 1984, the U.S. Department of Labor's Occupational Safety and Health Administration (OSHA) published a standard for ethylene oxide that established a permissible exposure limit of one part ethylene oxide per million parts of air determined as an eight hour time weighted average concentration (29 CFR 1910.1047, 49 FR 25734).

Ethylene oxide is a reactive chemical and there are a number of indicator devices available for visually monitoring ethylene oxide sterilization. Most of these devices use ink formulations which change color and indicate thereby that goods have been exposed to a sufficiently high ethylene oxide concentration for a sufficient time to cause sterilization. The ethylene oxide concentration is generally in the range of 600 to 900 milligrams per litre and exposure at elevated temperatures between 50 to 60 degrees C. for two or three hours is normal for sterilization. Most of these indicating devices are not sensitive to the one part per million eight hour time weighted average range required for monitoring worker exposure.

There are a number of devices available for environmental monitoring of ethylene oxide. Most of these devices are active in that they collect a sample of gas for the determination of the ethylene oxide concentration. One type of personal monitor consists of a battery powered pump worn by an individual, the pump drawing a measured volume of air into or through a collecting device which has an absorbent system such as activated charcoal. The activated charcoal is analyzed by normal analytical procedures.

Passive type dosimeters are available which include a badge or other device attached near a workers breathing zone. After exposure, these monitoring devices are re-sealed and returned to the manufacturer for analysis. A problem with such a device is the time delay between exposure and obtaining the results of the analysis. One daily personal monitor includes a badge worn by an individual who at the end of a work period places the badge in a developer solution and then, after a time delay, determines the time weighted average exposure to ethylene oxide using an electronic instrument. This system provides same day results of exposure to ethylene oxide, but it is not an instantaneous analysis.

The present invention provides an ethylene oxide monitoring device which is capable of measuring ethylene oxide dosage to less than one part per million for an eight hour time weighted average. The monitoring device is in the form of a passive monitoring device such as a dosimeter or badge which can be worn by an individual in a work area and then can be analyzed immediately after the work period to determine time weighted average exposure to ethylene oxide. The analysis does not require the use of an expensive electronic instrument. The badge indicates ethylene oxide dosage by means of color intensity change. This change is brought out by the addition of a developer. The developing process is substantially instantaneous thus avoiding the necessity of having to send the badge or dosimeter away and this allows a work area and/or an individual's personal exposure to be instantly checked for ethylene oxide concentration without having to return badges to the manufacturer's or other testing location for developing.

After the monitoring device in the form of a badge or dosimeter has been used, one drop of an alkaline solution is added to a reactive coating on the device and a blue dye is formed immediately. The intensity of the blue color is proportional to the time weighted average ethylene oxide dosage and the intensity of this color can be compared with a color comparison chart which has one reference color representing 1 ppm ethylene oxide concentration for an eight hour time weighted average.

Another feature of the dosimeter provides not only for the immediate indication of ethylene oxide dosage, but also provides for either storing or sending an undeveloped portion of the monitoring device to a control laboratory or other regulatory laboratory for a second test. The laboratory can develop the monitoring device under strict controls, and the ethylene oxide dosage determined as a back-up to confirm the initial indication.

The present invention provides an ethylene oxide monitoring device comprising a reactive coating sensitive to ethylene oxide on an impermeable substrate, the reactive coating including a layer of activated alumina particles, coated with p-nitrobenzyl pyridine and ammonium chloride adapted to instantly produce a color intensity change directly related to the time weighted average concentration of the reactive coating to ethylene oxide upon the addition of a developer.

In a preferred embodiment, a permeable attenuating barrier is provided over the reactive coating. In another embodiment, the reactive coating comprises a layer of activated alumina particles coated with polyvinyl alcohol, ammonium chloride and water, together with p-nitrobenzyl pyridine in a solvent solution. The p-nitrobenzyl pyridine is preferably in about 1–2% acetone solution. The activated alumina particles are preferred to be thin layer chromatography grade, and the impermeable substrate is preferably white, has a good rigidity and is chemically inert. A suitable material is a white polypropylene film.

The developer for the reactive coating is preferably an aqueous alkaline solution of 3% sodium hydroxide and is thickened with a cellulose-type thickener such as sodium carboxymethylcellulose. Alternatively, an alkanolamine such as an 85% aqueous solution of diethanolamine may be used. The permeable attenuating barrier is preferably a microporous polypropylene film, alternatively a coated paper with a U.V. absorber may be used. A foam layer may be positioned between the reactive coating on the impermeable substrate and the permeable attenuating barrier and a cavity is provided in the foam layer between the permeable, attenuating barrier and the reactive coating.

In yet another embodiment, the p-nitrobenzyl pyridine solution is contained in a squeezable reservoir with a channel to the reactive coating. The developer may be contained in another squeezable reservoir with a channel to the reactive coating. This provides a self-contained dosimeter.

The present invention also provides a method of determining time weighted average ethylene oxide concentration in an atmosphere comprising the steps of exposing a reactive coating sensitive to ethylene oxide to the atmosphere, the reactive coating including a layer of activated alumina particles coated with p-nitrobenzyl pyridine and ammonium chloride, adapted to instantly produce a color intensity change directly related to the time weighted average exposure concentration of the reactive coating to ethylene oxide, upon the addition of a developer, adding the developer to the reactive coating after exposure, and comparing the color intensity of the reactive coating with a color comparison means to determine if ethylene oxide dosage is above a predetermined level. The color comparison means is preferably a color comparison chart wherein different color intensities represent different time weighted average concentrations of ethylene oxide in the atmosphere, or is a meter which measures changes in color and intensity of color.

Referring now to the drawings:

FIG. 1 is an isometric view showing one embodiment of a passive monitoring device according to the present invention;

FIG. 2 is a cross sectional side elevation of the monitoring device shown in FIG. 1;

FIG. 3 is an isometric exploded view showing another embodiment of an ethylene oxide monitoring device;

FIG. 4 is a top view showing another embodiment of the monitoring device with reservoirs;

FIG. 5 is an isometric view showing another embodiment of a passive monitoring device according to the present invention;

FIG. 6 is an isometric exploded view showing the passive monitoring device of FIG. 5;

FIG. 7 is an isometric exploded view showing a still further embodiment of a passive monitoring device according to the present invention;

FIG. 8 is an isometric view showing the passive monitoring device of FIG. 7.

One example of an ethylene oxide monitoring device in the form of a badge or dosimeter 10 is shown in FIGS. 1 and 2. The dosimeter is a passive unit and has an impermeable substrate backing 11 which in one embodiment is an 8 mil thick polypropylene substrate. The substrate 11 is white, has good rigidity and is chemically inert to the developer used for bringing out the color intensity of the dosimeter. A reactive coating 12 is mounted on the substrate 11 at the center of the dosimeter 10. The reactive coating 12 has an activated alumina layer. Thin Layer Chromatography (TLC) grade activated alumina has been found to be the most suitable for the dosimeter. The activated alumina is mixed with water, polyvinyl alcohol as a binder, and ammonium chloride to enhance the color or sensitivity of the dosimeter. In one embodiment, a slurry of activated alumina in an aqueous solution of ammonium chloride and a binder is coated onto the substrate. When dry, a 1-2% solution of p-nitrobenzyl pyridine in solution is deposited on the activated alumina layer. Acetone is found to be a suitable solvent, however, other solvents such as methanol, benzene, ethanol and methylethylketone have also been used successfully. The activated alumina layer provides a large surface area for the p-nitrobenzyl pyridine so there can be a sufficient gas phase reaction for the ethylene oxide gas. Furthermore, activated alumina absorbs ethylene oxide gas.

During the drying of the coating, ammonium chloride dissociates to ammonia gas and hydrochloric acid. The gas dissipates and the acid changes the pH of the coating from alkaline to acidic. The reaction between ethylene oxide and p-nitrobenzyl pyridine is preferred at an acidic pH. It has been found that the preferred pH for the dried coating is in the range of about pH 3 to 6. As the pH of the coating is decreased below pH3, the coating is modified so that it is not uniformly activated by the p-nitrobenzyl pyridine solution. The preferred pH range for the coating is obtained by proper drying of the coating containing ammonium chloride, or by replacing the ammonium chloride with a mineral acid such as hydrochloric acid. Other acids such as nitric and sulfuric acids can also be used to adjust the pH of the coating formulation so that the final pH of the dried coating is in the preferred range. The presence of chloride ion in the coating appears to exert a synergistic effect on the sensitivity of the dosimeter. For example, dosimeters prepared from coating formulations with no ammonium chloride, but having pH adjusted to within the range of 3.0 to 3.5 with sulfuric acid plus sodium chloride, exhibit better sensitivity to ethylene oxide than dosimeters prepared from coatings whose pH has been adjusted with sulfuric acid, but with no sodium chloride. Whether the p-nitrobenzyl pyridine in solution is applied to the coating during production or immediately prior to use does not substantially affect the pH of the coating. To determine pH of the coating, a 200 mgm sample of dry coating was scraped off the dosimeter and suspended in 20 gm of distilled water. The pH of the solution was then determined after a 5 minute stirred extraction period.

A foam layer 15 is mounted on the substrate 11 and has a cavity 16 in the center over the reactive coating 12. A permeable attenuating barrier 17 is positioned over the cavity 16 and adheres to the foam layer 15 so there is a space over the reactive coating 12, the thickness of the foam layer 15 under the attenuating barrier 17. The purpose of the permeable attenuating barrier 17 is to reduce air velocity effects on the reactive coating 12 and to provide for diffusion of ethylene oxide to the absorbent activated alumina particles. Various permeable attenuating barriers 17 have been used, a microporous polypropylene such as that sold under the trade mark CELGARD 2400 has been used successfully. Microporous polypropylene films and other types of filter papers may also be used. Some of these attenuating films act as absorbers of ultraviolet radiation and this is an advantage inasmuch as ultraviolet radiation has been found to cause yellowing of the reactive coating which interferes with the color intensity changes from ethylene oxide exposure.

As can be seen in FIGS. 1 and 2, cut-outs 19 are provided in the foam layer 15 at opposing edges of the monitoring device 10. An impermeable cover 20 has a removable center strip 21 which is peeled off the attenuating barrier 17 in order to expose the monitoring device. This removable strip 21 seals the monitoring device and does not let atmospheric air pass to the reactive coating 12. The cut-out 19 is used for pulling off the removable strip 21 and the second cut-out 19 is used for stripping off the attenuating barrier 17 prior to adding the developer to the reactive coating. The cover 20 can have information such as reference and date written on a portion that is not part of the removable strip 21 so that the exact location and monitoring date are known.

In use, the dosimeter 10 is attached to an individual and is preferably located as close to the face of the individual as possible to sample the air at breathing height. An individual can wear the dosimeter 10 for a shift or for any period of time which is desired. The removable strip 21 is removed before the badge is attached to the worker. After the test period, the attenuating barrier 17 is removed and one drop of developer solution added in the cavity 16 to the reactive coating 12. The developer solution may be a 3% aqueous sodium hydroxide solution thickened with a cellulose type thickener such as sodium carboxymethylcellulose. An 85% aqueous solution of diethanolamine may also be used as a developer, as well as other alkanolamine solutions which extend the time that the developed color is stable. A blue color is produced immediately after the developer solution is added, provided the dosimeter has been exposed to ethylene oxide. The intensity of the blue color is proportional to the ethylene oxide exposure concentration, which is a function of exposure time and concentration of ethylene oxide in the atmosphere. For instance, if the concentration of ethylene oxide is low, but the exposure time long, then the intensity of color may be similar to a high concentration of ethylene oxide and short exposure time. However, a color reference may be prepared representing a selected ppm ethylene oxide 8 hour time weighted average exposure, such as 1 ppm, and the developed reactive coating compared with the color reference. If the coating is darker than the color reference, it indicates the dosimeter has been exposed to more than the selected ethylene oxide 8 hour time weighted average.

A color comparision chart may be prepared, which has different intensities of blue color representing different time weighted average ethylene oxide concentrations to which the dosimeter has been exposed. The color comparison chart allows for a quick indication of ethylene oxide dosage and if a more accurate figure is needed, then the color developed on the reactive coating can be measured with a meter which gives a signal representative of a particular color intensity. The color reference and the color comparison chart allows the user to determine the ethylene oxide dosage exposure without the need of sending the dosimeter 10 to a laboratory or other location.

In other embodiments, there may be two cavities 16, or alternatively, a portion of the reactive coating may have developer added so that the time weighted average ethylene oxide concentration can be initially determined and then the badge sent to a control laboratory where developer is added to the remaining undeveloped portion of the reactive coating under laboratory conditions and the time weighted average ethylene oxide concentration redetermined. This permits a check on the field test. It is preferable that the dosimeter is protected after the field test to avoid any chance of additional exposure to ethylene oxide.

FIG. 3 illustrates another embodiment of a monitoring device wherein the foam layer 15 has a carrier portion 30 which is not connected to the impermeable substrate 11, and which may be peeled off the back of the foam layer 15 leaving an adhesive area that can be used for attaching the monitoring device to the clothing of an individual. The cavity 16 is positioned over the reactive coating 12 and an upper cover 31 remains attached to the foam layer 15 when the removable cover strip 21 is removed. This upper cover 31 can have information written thereon relating to the date and use of the dosimeter.

The p-nitrobenzyl pyridine solution may be deposited on the activated alumina coating at the time of use. If the dosimeter is stored without the p-nitrobenzyl pyridine solution in the coating, then the dosimeter's shelf life is extended. The solution may be added from a dropper, or alternatively, a built-in reservoir is formed in the dosimeter as shown in FIG. 4. In this embodiment, the reactive coating 12 which comprises activated alumina, polyvinyl alcohol and ammonium chloride is placed in a pocket 40 in a foam substrate 41. A first reservoir 43, being a cavity in the foam substrate 41 contains a solution of p-nitrobenzyl pyridine and has a channel 44 feeding to the pocket 40. The cavity in the foam layer is sealed on both sides so the liquid is contained therein. To activate the dosimeter 10, the first reservoir 43 is squeezed so the solution passes along the channel 44 and is deposited on the activated alumina coating in the pocket. The dosimeter may be kept in a sealed pouch or other sealed container prior to use.

To determine the ethylene oxide dosage after the test period, a second reservoir 45 is provided in the foam substrate 41 containing the developer. When the second reservoir 45 is squeezed, developer solution passes through channel 46 and is deposited on the reactive coating in the pocket 40. The dosimeter 10 has the advantage of being a completely self contained unit not requiring the addition of any other additives. It is merely necessary to compare the developed reactive coating wit a color reference to determine whether it is lighter or darker than the reference.

Another embodiment of a dosimeter 10 is shown in FIGS. 5 and 6, wherein a two sided adhesive tape 51 is positioned on top of the foam layer 15 and has a release liner 52 on the tape 51. In use, the release liner 52 is removed after the activated alumina in the reactive coating 12 has been activated with the p-nitrobenzyl pyridine solution. The attenuating barrier 17 can then be adhered to the adhesive surface of the two sided tape 51.

A still further embodiment of a dosimeter 10 is shown in FIGS. 7 and 8. A cardboard holder 60 has a round exposure aperture 61 and a flap 62 which folds over, similar to a book of matches, and has an end piece 63 fitting through a slot 64 in the end of the holder 60. The reactive coating 12 is on a polypropylene substrate 11 which fits into the holder 60. An insert which comprises the foam layer 15 with the attenuating barrier 17 laminated thereon. The insert can be removed from the holder 60 to apply the p-nitrobenzyl pyridine in acetone solution to the coating 12 and thus activate the dosimeter. The insert is inserted for exposure measurement, and then removed after use for applying the developer to the coating 12.

A chemical thermal paper 65 is included adjacent to the reactive coating 12. The color of the paper changes when the p-nitrobenzyl pyridine in acetone solution is added, the acetone vapour or liquid causing the color change, thus showing that the dosimeter has been activated and avoiding incorrect test results if the developer were added and the dosimeter had not been activated.

Various changes may be made to the embodiments shown herein without departing from the scope of the present invention which is limited only by the following claims.

The embodiments of our invention in which an exclusive property or privilege is claimed are defined as follows:

1. An ethylene oxide monitoring device comprising a reactive coating sensitive to ethylene oxide on an impermeable substrate, the reactive coating including a layer of activated alumina particles, coated with p-nitrobenzyl pyridine and ammonium chloride, adapted to instantly produce a color intensity change directly related to the exposure of the reactive coating to ethylene oxide upon addition of a developer, the color intensity change indicating an exposure sensitivity less than one ppm for an eight hour time weighted average.

2. The monitoring device according to claim 1 including color comparison means to compare color of developed reactive coating therewith to determine ethylene oxide dosage.

3. The monitoring device according to claim 1 in the form of a badge for attachment to a person.

4. The monitoring device according to claim 1 wherein the p-nitrobenzyl pyridine in an acetone solution is added to the coating prior to commencing to measurement weighted average ethylene oxide dosage.

5. The monitoring device according to claim 4 including a chemical thermal paper strip on the device which changes color when the p-nitrobenzyl pyridine in an acetone solution is added to show that the device has been activated to measure time weighted average ethylene oxide dosage.

6. The monitoring device according to claim 1 including a squeezable reservoir in the device, the reservoir containing the developer with a channel to the reactive coating.

7. The monitoring device according to claim 6 wherein the p-nitrobenzyl pyridine solution is contained in a squeezable reservoir with a channel to the reactive coating.

8. The monitoring device according to claim 1 wherein the reactive coating has a pH in the approximate range of 3 to 6 before application of the developer.

9. The monitoring device according to claim 8 wherein the reactive coating comprises a layer of activated alumina particles, coated with polyvinyl alcohol, ammonium chloride and water together with p-nitrobenzyl pyridine in a solvent solution.

10. The monitoring device according to claim 8 wherein the reactive coating comprises a layer of activated alumina particles, coated with polyvinyl alcohol; an acid selected from the group consisting of hydrochloric acid, nitric acid and sulphuric acid; and water together with p-nitrobenzyl pyridine in a solvent solution.

11. The monitoring device according to claim 8 wherein the reactive coating comprises a layer of activated alumina particles, coated with polyvinyl alcohol; mineral acid; chloride salt and water together with p-nitrobenzyl pyridine in a solvent solution, the reactive coating having a pH in the approximate range of 3.0 to 6.0 before addition of the developer.

12. The monitoring device according to claim 1 wherein a permeable attenuating barrier is provided over the reactive coating.

13. The monitoring device according to claim 12 wherein the permeable attenuating barrier is a microporous polypropylene film.

14. The monitoring device according to claim 12 wherein a foam layer is positioned between the reactive coating on the impermeable substrate and the permeable attenuating barrier, and a cavity is provided in the foam layer between the permeable attenuating barrier and the reactive coating.

15. The monitoring device according to claim 14 including a removable impermeable cover placed over the permeable attenuating barrier to seal the reactive coating before exposure.

16. The monitoring device according to claim 14 wherein a first squeezable reservoir containing the p-nitrobenzyl pyridine solution is located in the foam layer, having a first channel to the reactive coating, and a second squeezable reservoir containing the developer is located in the foam layer, having a second channel to the reactive coating.

17. The monitoring device according to claim 1 wherein the reactive coating comprises a layer of activated alumina particles, coated with polyvinyl alcohol, ammonium chloride and water together with p-nitrobenzyl pyridine in a solvent solution.

18. The monitoring device according to Cl.iam 17 wherein the p-nitrobenzyl pyridine is in about 1-2% acetone solution.

19. The monitoring device according to claim 17 wherein the activated alumina particles are thin layer chromatography grade.

20. The monitoring device according to claim 17 wherein the developer is an aqueous alkanolamine solution.

21. The monitoring device according to claim 17 wherein the impermeable substrate is white, has good rigidity, and is chemically inert.

22. The monitoring device according to claim 21 wherein the impermeable substrate is a white polypropylene film.

23. The monitoring device according to claim 17 wherein the developer is an aqueous alkaline solution of sodium hydroxide.

24. The monitoring device according to claim 23 wherein the sodium hydroxide is about a 3% solution and is thickened with a cellulose-type thickener.

25. The monitoring device according to claim 24 wherein the thickener is sodium carboxymethylcellulose.

26. A method of determining time weighted average ethylene oxide dosage, comprising the steps of:
exposing a reactive coating sensitive to ethylene oxide to the atmosphere, the reactive coating including a layer of activated alumina particles coated with p-nitrobenzyl pryidine and ammonium chloride, adapted to instantly produce a color intensity change directly related to the exposure of the reactive coating to ethylene oxide upon addition of a developer, the color intensity change indicating an exposure sensitivity less than one ppm for an eight hour time weighted average;
adding the developer to the reactive coating after exposure; and
comparing the color intensity of the reactive coating with a color comparison means to determine if time weighted average ethylene oxide dosage is above a predetermined level.

27. The method according to claim 26 wherein the developer is added to a portion of the reactive coating initially and the color intensity compared on the portion of the coating, the remaining portion of the coating being developed at a later time and the color intensity compared.

28. The method according to claim 26 wherein the reactive coating has a pH in the approximate range of 3 to 6 before application of the developer.

29. The method according to claim 26 wherein the reactive coating is prepared without the p-nitrobenzyl pyridine in a solvent solution and has a pH in the approximate range of 3 to 6, and the p-nitrobenzyl pyridine in a solvent solution is applied prior to exposing the reactive coating to the atmosphere for determining ethylene oxide dosage.

30. The method according to claim 26 wherein the reactive coating is covered with a permeable cover prior to exposure to the atmosphere.

31. The method according to claim 26 wherein the color comparison means is a color comparison chart and different color intensities represent different time weighted average dosage of ethylene oxide in the atmosphere.

32. The method according to claim 26 wherein the color comparison means is a meter to measure change in color and intensity of color.

33. The method according to claim 26 wherein the reactive coating is applied to an impermeable substrate which is white, has good rigidty and is chemically inert.

34. The method according to claim 33 wherein the impermeable substrate is a white polypropylene film.

35. The method according to claim 26 wherein the reactive coating comprises a layer of activated alumina particles, coated with polyvinyl alcohol, ammonium chloride and water together with p-nitrobenzyl pyridine in a solvent solution.

36. The method according to claim 35 wherein the p-nitrobenzyl pyridine is in about 1 to 2% acetone solution.

37. The method according to claim 35 wherein the activated alumina particles are thin-layer chromatography grade.

38. The method according to claim 26 wherein the developer is an aqueous alkaline solution of sodium hydroxide.

39. The method according to claim 38 wherein the sodium hydroxide is about a 3% solution and is thickened with a cellulose type thickener.

40. The method according to claim 38 wherein the thickener is a sodium carboxymethylcellulose.

41. The method according to claim 26 including covering the reactive coating with a permeable attenuating barrier before exposure to the atmosphere.

42. The method according to claim 41 wherein the attenuating barrier is a microporous polpropylene film.

43. The method according to claim 41 wherein the attenuating barrier is spaced from the reactive coating by a foam layer.

* * * * *